United States Patent [19]

Vincze et al.

[11] Patent Number: 5,223,626
[45] Date of Patent: Jun. 29, 1993

[54] PREPARATION OF CATIONIC ALKYLENEDIAMINE DYE INTERMEDIATES

[75] Inventors: Janos Vincze, Basle, Switzerland; Wilfried Herter, Rheinfelden, Fed. Rep. of Germany

[73] Assignee: Ciba-Geigy Corporation, Ardsley, N.Y.

[21] Appl. No.: 437,719

[22] Filed: Nov. 16, 1989

[30] Foreign Application Priority Data

Nov. 21, 1988 [CH] Switzerland ............... 4315/88

[51] Int. Cl.⁵ ............... C07D 213/127; C07C 213/08; C07C 241/02; C07C 215/90
[52] U.S. Cl. ................... 546/329; 564/282; 564/290; 564/291; 564/295; 564/296
[58] Field of Search ............... 546/329; 564/290, 295, 564/296, 282, 291

[56] References Cited

U.S. PATENT DOCUMENTS

| | | | |
|---|---|---|---|
| 2,099,525 | 11/1937 | Krzikalla et al. | 534/603 X |
| 3,658,781 | 4/1972 | Hegar | 546/329 |
| 4,695,632 | 9/1987 | Kalk et al. | 544/194 |

FOREIGN PATENT DOCUMENTS

| | | | |
|---|---|---|---|
| 2548879 | 5/1976 | Fed. Rep. of Germany | 534/606 |
| 0547337 | 3/1974 | Switzerland | 537/606 |
| 1047293 | 3/1965 | United Kingdom | 534/606 |
| 1533126 | 7/1976 | United Kingdom | 534/606 |
| 1520423 | 11/1978 | United Kingdom | 534/606 |
| 1551613 | 8/1979 | United Kingdom . | |

OTHER PUBLICATIONS

Tong et al., J. Amer. Chem. Soc., vol. 82, pp. 1988 to 1996, (1960).
R. L. Bent J. Am. Chem. 73, 3100–3123, (1951).

*Primary Examiner*—Floyd D. Hidel
*Assistant Examiner*—MarySusan H. Gabilan
*Attorney, Agent, or Firm*—Kevin T. Mansfield; Edward McC. Roberts

[57] ABSTRACT

Compounds of the formula

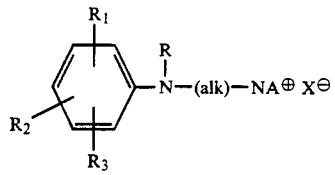

(1)

where $R_1$, $R_2$ and $R_3$ are each independently of the others hydrogen, $C_1$–$C_4$alkyl, $C_1$–$C_4$alkoxy, halogen or $C_1$–$C_4$alkanoylamino, R is hydrogen or unsubstituted or $C_1$–$C_4$alkoxy substituted $C_1$–$C_{12}$alkyl or an —(alk)—NA⊕X⊖ radical or, R forms together with an $R_1$ in the ortho-position relative to the amino group a partially hydrogenated, substituted or unsubstituted 5- to 7-membered heterocyclic ring which may contain additional N, S or O atoms as ring members, (alk) is a substituted or unsubstituted $C_1$–$C_6$alkylene radical, —NA⊕ is the radical of an amino compound of formula

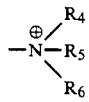

(2)

or

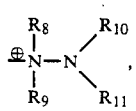

(2')

where $R_4$, $R_5$ and $R_6$ are each independently of the others substituted or unsubstituted $C_1$–$C_6$alkyl, substituted or unsubstituted $C_7$–$C_{12}$aralkyl or substituted or unsubstituted aryl, $R_8$ and $R_9$ are each independently of the other substituted or unsubstituted $C_1$–$C_6$alkyl, and $R_{10}$ and $R_{11}$ are each independently of the other hydrogen, substituted or unsubstituted $C_1$–$C_6$alkyl, substituted or unsubstituted $C_7$–$C_{12}$aralkyl or substituted or unsubstituted aryl, or is the positively charged radical of a 5- to 7-membered aliphatic or aromatic heterocycle which may contain additional N, S or O atoms as ring members, and $X^\ominus$ is a halide ion, are prepared by reacting a compound of the formula

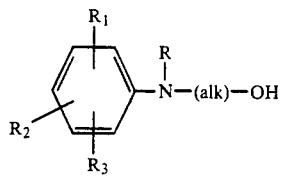

(3)

with a halogenating agent in the presence of a compound of the formula

NA  (2a)

where the symbols are as defined in claim 1, these compounds being useful coupling components for the synthesis of cationic dyes.

19 Claims, No Drawings

PREPARATION OF CATIONIC ALKYLENEDIAMINE DYE INTERMEDIATES

The present invention relates to a process for preparing cationic coupling components and to the use thereof for synthesizing cationic azo dyes.

It is already known, for example from L. K. J. Tong et al., J. Am. Chem. Soc. 82, 1988-96 (1960), to prepare N-[2-(N-ethyl-3-methylanilino)ethyl]pyridinium chloride by chlorination of N-ethyl-N-(2-hydroxyethyl)-3-methylaniline with phosphoryl chloride (POCl₃), isolation of the resulting chloroethyl compound, and subsequent reaction with pyridine. This 2-stage process is complicated and, owing to the intermediate isolation, produces only a low overall yield; furthermore, practice of the process on an industrial scale is problematical on account of the highly exothermic nature of the chlorination reaction.

It has now been found, surprisingly, that corresponding cationic coupling components can be prepared in improved yield and higher safety in a one-pot process.

The present invention accordingly provides a process for preparing a compound of the formula

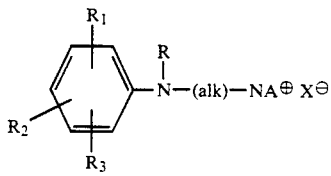 (1)

where $R_1$, $R_2$ and $R_3$ are each independently of the others hydrogen, $C_1$-$C_4$alkyl, $C_1$-$C_4$alkoxy, halogen, trifluoromethyl or $C_1$-$C_4$alkanoylamino, R is hydrogen, substituted or unsubstituted $C_1$-$C_{12}$alkyl or an —(alk)—NA⊕X⊖ radical, or R forms together with an $R_1$ in the ortho-position relative to the amino group a partially hydrogenated, substituted or unsubstituted 5- to 7-membered heterocyclic ring which may contain additional N, S or O atoms as ring members, (alk) is a substituted or unsubstituted $C_1$-$C_6$alkylene radical,
—NA⊕ is the radical of an amino compound of formula

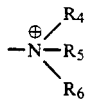 (2)

or

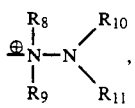 (2')

where $R_4$, $R_5$ and $R_6$ are each independently of the others substituted or unsubstituted $C_1$-$C_6$alkyl, substituted or unsubstituted $C_7$-$C_{12}$aralkyl or substituted or unsubstituted aryl, $R_8$ and $R_9$ are each independently of the other substituted or unsubstituted $C_1$-$C_6$alkyl, and $R_{10}$ and $R_{11}$ are each independently of the other hydrogen, substituted or unsubstituted $C_1$-$C_6$alkyl, substituted or unsubstituted $C_7$-$C_{12}$aralkyl or substituted or unsubstituted aryl, or is the positively charged radical of a 5-7-membered aliphatic or aromatic heterocycle which may contain additional N, S or O atoms as ring members, and X⊖ is a halide ion, which comprises reacting a compound of the formula

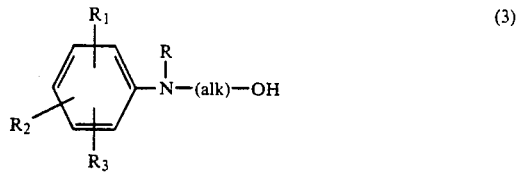 (3)

with a halogenating agent in the presence of a compound of the formula

NA (2a)

with liberation of an anion X⊖ and with R, $R_1$, $R_2$, $R_3$ and (alk) in the formula (3) each being as defined above and NA being the uncharged parent nitrogen compound to the radical —NA⊕.

A $C_1$-$C_4$alkyl $R_1$, $R_2$ or $R_3$ is generally methyl, ethyl, n-propyl, isopropyl, n-butyl, isobutyl, sec-butyl or tert-butyl.

A $C_1$-$C_4$alkoxy $R_1$, $R_2$ or $R_3$ may in general be methoxy, ethoxy, n-propoxy, isopropoxy, n-butoxy, isobutoxy, sec-butoxy or tert-butoxy.

A halogen $R_1$, $R_2$ or $R_3$ is for example iodine, bromine, fluorine or preferably chlorine.

A $C_1$-$C_4$alkanoylamino $R_1$, $R_2$ or $R_3$ is for example propionylamino or preferably acetylamino.

Preferred meanings of $R_1$, $R_2$ and $R_3$ are: hydrogen, methyl, ethyl, methoxy, ethoxy, chlorine, acetylamino, propionylamino.

Particularly preferably, one of $R_1$, $R_2$ and $R_3$ is hydrogen and the other two are each independently of the other hydrogen, methyl, chlorine or acetylamino.

In a particularly preferred embodiment of the process according to the invention, two of $R_1$, $R_2$ and $R_3$ are each hydrogen while the third one is hydrogen, methyl or chlorine.

An alkyl R can be for example methyl, ethyl, n-propyl, isopropyl, n-butyl, sec-butyl, isobutyl, tert-butyl or straight-chain or branched pentyl, hexyl, heptyl, octyl, nonyl, decyl, undecyl or dodecyl, which may each be substituted for example by $C_1$-$C_4$alkoxy.

Preferably, R is hydrogen or an unsubstituted $C_1$-$C_6$alkyl, particularly preferably it is hydrogen or $C_1$-$C_4$alkyl, and very particularly preferably it is hydrogen, methyl or ethyl.

The complement to a partially hydrogenated heterocyclic ring formed by $R_1$ and $R_2$ together with the N atom leads for example to a 5- to 7-membered heterocycle with one or more double bonds which is fused to the benzene ring and contains one or two N atoms or an N atom and an S or O atom. Such a heterocycle may also be substituted, for example by $C_1$-$C_4$alkyl, $C_1$-$C_4$alkoxy or halogen, but in particular by $C_1$-$C_4$alkyl. The number of alkyl groups here may be 1 to 6, for example 1 to 5, in particular 1 to 4, particularly preferably 1 to 3; particular preference is given here to methyl groups.

For example, R and $R_1$ together with the N atom and the fused-on benzene ring form an unsubstituted or $C_1$-$C_4$alkyl-monosubstituted to -pentasubstituted dihydroindole, tetrahydroquinoline, tetrahydroquinoxaline or tetrahydro-1,4-benzoxazine radical, of which the dihydroindole and the tetrahydroquinoline radicals are preferred.

(alk) is for example methylene, ethylene, 1,3-propylene, 1,4-butylene, 1,5-pentylene or 1,6-hexylene or a branched isomer thereof, which may each be substituted for example by $C_1$-$C_4$alkoxy, $C_1$-$C_4$alkanoyloxy, $C_1$-$C_4$alkoxycarbonyl or carbamoyl. Preferably, (alk) is $C_2$-$C_4$alkylene, in particular 1,2- or 1,3-propylene or ethylene, especially ethylene.

A $C_1$-$C_6$alkyl $R_4$, $R_5$ or $R_6$ can be methyl, ethyl, n-propyl, isopropyl, n-butyl, isobutyl, sec-butyl or tert-butyl or a straight-chain or branched pentyl or hexyl, which may each be substituted, for example by hydroxyl, $C_1$-$C_4$alkoxy, $C_1$-$C_4$alkanoyloxy, $C_1$-$C_4$alkoxycarbonyl or carbamoyl. Preferably, this $C_1$-$C_6$alkyl is unsubstituted or hydroxyl-substituted $C_1$-$C_4$alkyl, in particular methyl or ethyl.

Alkyls $R_4$, $R_5$ and $R_6$ may differ from one another or preferably be identical.

Aryl $R_4$, $R_5$ or $R_6$ can be for example unsubstituted phenyl or phenyl which is substituted, for example by hydroxyl, $C_1$-$C_4$alkyl, $C_1$-$C_4$alkoxy, halogen, $C_1$-$C_4$alkanoylamino, $C_1$-$C_4$alkylsulfonyl, sulfamoyl, nitro, cyano and/or carbamoyl.

Aryl $R_4$, $R_5$ or $R_6$ is preferably unsubstituted or methyl-, methoxy-, chlorine- or acetylamino-substituted phenyl.

Aralkyl $R_4$, $R_5$ or $R_6$ can be for example benzyl or phenylethyl, which may each be substituted, for example as described for aryl.

Aralkyl $R_4$, $R_5$ or $R_6$ is preferably unsubstituted or methyl-, methoxy-, chlorine- or acetylamino-substituted benzyl, particularly preferably unsubstituted benzyl.

$R_8$ and $R_9$ are each independently of the other subject to the definitions and preferences indicated above for substituted or unsubstituted $C_1$-$C_6$alkyl $R_4$.

$R_8$ and $R_9$ are different or preferably identical, each being particularly preferably methyl or ethyl.

Substituted or unsubstituted $C_1$-$C_6$alkyl, substituted or unsubstituted $C_7$-$C_{12}$alkyl and substituted or unsubstituted aryl $R_{10}$ or $R_{11}$ is subject independently of the others to the definitions and preferences indicated above for $R_4$.

$R_{10}$ and $R_{11}$ are different or preferably identical, each being particularly preferably hydrogen.

A radical $-NA^\oplus$ of an aliphatic heterocycle may be derived for example from an N-alkylated piperidine, morpholine, tetrahydropyrrole, dihydropyrazole or oxazolidine. Preferably $-NA^\oplus$ is the radical

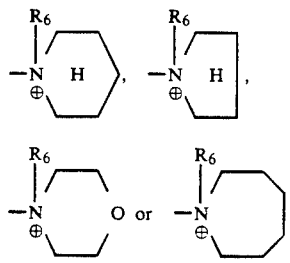

where $R_6$ is subject to the abovementioned definitions and preferences.

A radical $-NA^\oplus$ of an aromatic heterocycle may be derived for example from one of the following heterocyclic compounds: pyrrol, indole, pyrazole, imidazole, benzimidazole, oxazole, benzoxazole, thiazole, benzothiazole, 1,2,4- or 1,3,4-thiadiazole, 1,2,3- or 1,2,4-triazole, benzotriazole, pyridine, pyrimidine, pyrazine, quinoline or isoquinoline, each of which compounds may be substituted, for example by $C_1$-$C_4$alkyl, $C_1$-$C_4$alkoxy, carbamoyl or halogen and must not contain any hydrogen atom bonded to a ring nitrogen atom; such nitrogen atoms, for example in pyrrol, indole, pyrazole, imidazole or triazole, are substituted for example by $C_1$-$C_4$alkyl, unsubstituted phenyl or phenyl which is substituted as described above.

A group $-NA^\oplus$ in the formula (1) derived from an aromatic heterocycle preferably conforms to the formula

 (4)

where $R_7$ is hydrogen, methyl or carbamoyl; particularly preferably, a $-NA^\oplus$ radical derived from an aromatic heterocycle is pyridinium or o-, m- or p-methylpyridinium.

$X^\ominus$ is for example $I^\ominus$, $Br^\ominus$ or in particular $Cl^\ominus$.

The process according to the invention is suitable for example for preparing compounds of the formula

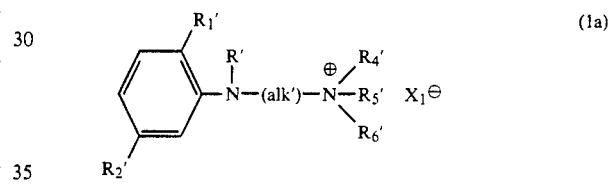 (1a)

especially compounds of the formula

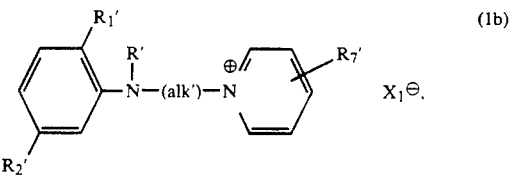 (1b)

where $R_1'$ and $R_2'$ are each independently of the other hydrogen, methyl, chlorine or acetylamino, $R'$ is hydrogen or $C_1$-$C_4$alkyl, (alk') is straight-chain or branched $C_2$-$C_4$alkylene, $R_4'$, $R_5'$ and $R_6'$ are each independently of the others unsubstituted or hydroxyl-substituted $C_1$-$C_4$alkyl or unsubstituted or methyl-, methoxy-, chlorine- or acetylamino-substituted benzyl, $R_7'$ is hydrogen or methyl, and $X_1^\ominus$ is a bromide ion or in particular a chloride ion.

The halogenating agent used for the process according to the invention can be any one of the halogenating reagents customarily used for the halogenation of alkyl hydroxides; the first possibility is an inorganic acid halide, for example of the formula $PX_3$, $PX_5$, $POX_3$, $SOX_2$ or $SO_2X_2$, or an organic acid halide, for example of the formula $R_{12}$—$SO_2$—$X$ or

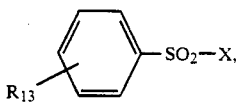

where X is in either case halogen, $R_{12}$ is $C_1$–$C_4$alkyl and $R_{13}$ is for example hydrogen, $C_1$–$C_4$alkyl, $C_1$–$C_4$alkoxy, halogen or nitro. Preference is given in particular to those abovementioned inorganic and organic halogenating agents where X is chlorine, $R_{12}$ is methyl or ethyl and $R_{13}$ is hydrogen, methyl, chlorine, bromine or nitro.

Examples of suitable halogenating agents are: phosphorus trichloride ($PCl_3$), phosphorus pentachloride ($PCl_5$), phosphoryl chloride ($POCl_3$), thionyl chloride ($SOCl_2$), sulfuryl chloride ($SO_2Cl_2$), methanesulfonyl chloride, p-chlorobenzenesulfonyl chloride, p-bromophenylsulfonyl chloride, p-toluenesulfonyl chloride, m- or p-nitrophenylsulfonyl chloride, benzenesulfonyl chloride and the corresponding iodine and bromine compounds.

Besides these, it is also possible to use mixtures of two or more halogenating agents, for example a mixture of $POCl_3$ and thionyl chloride.

Preferred halogenating agents are $PCl_3$, $PCl_5$, $POCl_3$, methanesulfonyl chloride, benzenesulfonyl chloride, and p-toluenesulfonyl chloride with the use of $POCl_3$ being particularly preferred.

The halogenating agent is generally used in such an amount that the amount of halogen atom X or halide ion $X^\ominus$ present relative to the compound of the formula (3) is at least equivalent and preferably excessive to a certain degree.

The amount of halogenating agent is advantageously determined in such a way that it contains at least one equivalent and preferably 1 to 3 equivalents of halogen atom X or halide ion $X^\ominus$ per equivalent of compound of the formula (3).

For instance, the amount per mole of compound of the formula (3) is for example 0.33 to 1.0 mole, preferably 0.35 to 0.6 mole, particularly preferably 0.4 to 0.5 mole, of a compound of the formula $PX_3$ or $POX_3$, where X is in either case as defined above.

The compounds of the formula (2a) are the uncharged parent nitrogen compounds NA to the radical —$NA^\oplus$; they, like the compounds of formula (3), are known per se or can be obtained in a manner known per se.

The nitrogen compound of the formula (2a) is in general used in excess, based on the compound of the formula (3), the molar ratio being for example 1.5:1 to 10:1, preferably 2:1 to 5:1, particularly preferably 2:1 to 3.5:1. It is also possible to use mixtures of different compounds of formula (2a). Finally, it can be advisable, in particular in the case of low-boiling compounds of the formula (2a), to use in addition to a compound of the formula (2a) an inert solvent, for example an aliphatic or aromatic hydrocarbon or preferably a dipolar aprotic solvent. Suitable aliphatic and aromatic hydrocarbons are for example straight-chain and branched alkanes and alkane mixtures (petroleum ethers, naphthas), toluene, o-, m- or p-xylene and xylene mixtures. Suitable dipolar aprotic solvents are for example: formamide, N-methylformamide, N,N-dimethylformamide, N-methylpyrrolidone, dimethyl sulfoxide, sulfolane, chlorobenzene, 1-chloronaphthalene, ethylene glycol dimethyl ether, ethylene glycol diethyl ether, and diethylene glycol dimethyl ether. It is also possible to use mixtures of various solvents. But it is preferable not to use any additionally solvent in the process.

The process according to the invention is advantageously carried out by introducing the hydroxy compound of the formula (3) and the nitrogen compound of the formula (2a) into a reaction vessel as initial charge, for example at room temperature, and adding the halogenating agent; the rate of addition of halogenating agent is regulated in such a way that the temperature of the reaction mixture does not exceed a value of for example 150° C., preferably 140° C.

It must be considered a particular advantage of the process according to the invention that, owing to the presence of the nitrogen compound of the formula (2a), the temperature control of this exothermic reaction does not present a problem, even with large batches, and can be effected without special cooling measures, for example using air cooling alone.

The length of time for the dropwise addition of the halogenating agent depends strongly on the batch size, and can range for example from 15 minutes to 5 hours, preferably from 20 to 60 minutes, in particular from 25 to 45 minutes.

After the halogenating agent has been added, the reaction is allowed to go to completion, in general at elevated temperature, for example at 60° to 200° C., preferably at 75° to 150° C. and in particular at 100° to 150° C.; preferably the reaction mixture is refluxed for the duration, which depends on the starting materials but which in general ranges for example from 2 to 24 hours, preferably from 5 to 20 hours and in particular from 8 to 15 hours.

The compound of the formula (1) obtained by the process is then conventionally isolated and purified, for example by removing the liquid organic constituents of the reaction mixture by distillation, taking up the product in water and if necessary subjecting it to a steam distillation.

A preferred embodiment of the present invention relates to a process for preparing a compound of the abovementioned formula (1) where $R_1$, $R_2$ and $R_3$ are each independently of the others hydrogen, methyl, ethyl, methoxy, ethoxy, chlorine, acetylamino or propionylamino, R is hydrogen or $C_1$–$C_6$alkyl, (alk) is $C_2$–$C_4$alkylene, —$NA^\oplus$ is a) a radical of the abovementioned formula (2) where $R_4$, $R_5$ and $R_6$ are each independently of the others unsubstituted or hydroxyl-substituted $C_1$–$C_4$alkyl or unsubstituted or methyl-, methoxy-, chlorine- or acetylamino-substituted benzyl or phenyl, b) a radical of the formula

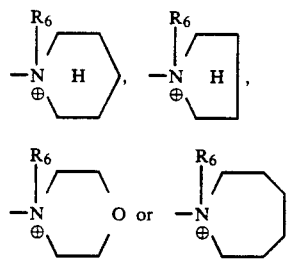

where $R_6$ is $C_1$–$C_4$alkyl, or c) an unsubstituted or $C_1$–$C_4$alkyl-, $C_1$–$C_4$alkoxy-, carbamoyl- or halogen-substituted positively charged pyrrole, indole, pyrazole, imidazole, benzimidazole, oxazole, benzoxazole, thiazole, benzothiazole, 1,2,4- or 1,3,4-thiadiazole, 1,2,3-

1,2,4-triazole, benzotriazole, pyridine, pyrimidine, pyrazine, quinoline or isoquinoline radical, and $X^{\ominus}$ is an iodide, bromide or chloride ion, wherein a compound of the formula

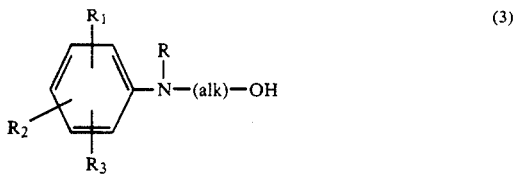     (3)

and a compound of the formula

NA     (2a), where R, $R_1$, $R_2$, $R_3$ and (alk) are each as defined above and NA is the uncharged parent nitrogen compound to the radical $-NA^{\oplus}$, are introduced as initial charge into a reaction vessel at room temperature, a halogenating agent of the formula $PX_3$, $PX_5$, $POX_3$, $SOX_2$ or $SO_2X_2$, where X is iodine, bromine or chlorine is added in such a way that the temperature of the reaction mixture does not exceed 150° C., and the reaction is allowed to go to completion at 75° to 150° C.

A particularly preferred embodiment of the present invention relates to a process for preparing a compound of the formula

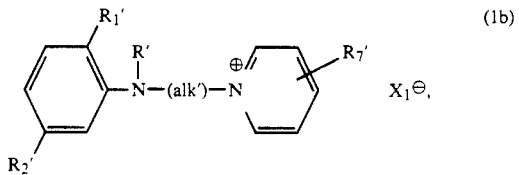     (1b)

where R', $R_1'$, $R_2'$, $R_7'$, (alk') and $X_1^{\ominus}$ are each as defined above, wherein a compound of the formula

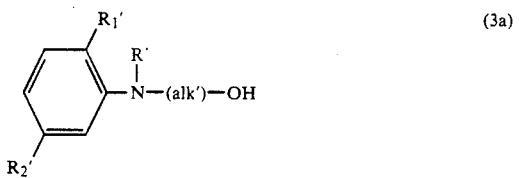     (3a)

and a compound of the formula

     (4a)

are introduced as initial charge into a reaction vessel at room temperature, a halogenating agent $POX_3$ is added in such a way that the temperature of the reaction mixture does not exceed 150° C., and the reaction is allowed to go to completion at 100° to 150° C., R', $R_1'$, $R_2'$, $R_7'$ and (alk') in the formulae (3a) and (4a) each being as defined above and X being bromine or in particular chlorine.

The novel one-pot process for preparing cationic coupling components has the abovementioned advantages of safety over conventional 2-stage processes, but also economic and ecological advantages, which are all due to the fact that intermediary isolation is dispensed with and the starting materials are reacted in a one-pot process.

This is because an intermediary isolation consumes solvent, energy, for example for a distillation, and time, and severely reduces the overall yield. In addition, little halogenating agent is required in the process according to the invention; the saving in halogenating agent compared with the existing 2-stage processes is about 50% or more. It consequently follows that the process according to the invention makes it possible to prepare cationic coupling components in a high yield in a simple and safe manner, i.e. very economically. The compounds of the formula (1) are useful intermediates, useable in particular as coupling components for the preparation of cationic dyes in a conventional manner. The dyes obtained, which are known per se, are suitable for dyeing for example acid-modified synthetic fibres, in particular those made of polyacrylonitrile material, producing dyeings having excellent allround fastness properties.

In the Examples which follow, parts and percentages are by weight and the temperatures are in degrees Celsius.

EXAMPLE 1

A stirred flask is charged with 165.2 parts of N-ethyl-N-(2-hydroxyethyl)aniline and 205.7 parts of pyridine at room temperature, and 69 parts of phosphoryl chloride ($POCl_3$) are added dropwise; in the course of the dropwise addition, which takes about 30 to 35 minutes, the temperature rises to 130°-135° C.

After all the $POCl_3$ has been added, the reaction mixture is refluxed for about 10 hours (temperature about 130°-135° C.). Excess pyridine is then distilled off under a slightly reduced pressure, and the resulting crude product of the formula

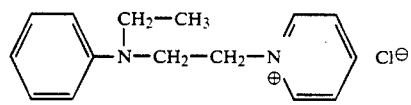

is worked up in a conventional manner or diluted with water and directly processed into the corresponding dye; the yield of cationic coupling component is almost quantitative, and the space-time yield is excellent.

COMPARATIVE EXAMPLE 1

The reaction described in Example 1 is carried out as a 2-stage process by first reacting N-ethyl-N-(2-hydroxyethyl)aniline with $POCl_3$ (about twice the amount required compared with Example 1 to keep the mixture stirrable), isolating the resulting chloroethyl compound and then reacting it with pyridine. The same pyridinium compound as in Example 1 is obtained, except the space-time yield is half that of the process of Example 1; that is, given reaction vessels of equal size, only half as much pyridinium compound is obtained per unit time than by the method of Example 1.

EXAMPLE 1a

A stirred flask is charged with 165.2 parts of N-ethyl-N-(2-hydroxyethyl)-aniline at room temperature; a solution of 62.5 parts of phosphorus pentachloride ($PCl_5$) in 600 parts of pyridine is added dropwise in the course of about 30 minutes, during which the temperature rises to about 70° C. The mixture is then heated at 100° C. for 1 hour. 300 parts of pyridine are then distilled off under a slightly reduced pressure by gradually raising the temperature, and the reaction mixture is then refluxed for about 10 hours (temperature about 130°–135° C.). The working-up is carried out as described in Example 1 and gives the same pyridinium compound in a similar space-time yield.

EXAMPLE 1b

A stirred flask is charged with 165.2 parts of N-ethyl-N-(2-hydroxyethyl)aniline and 261 parts of pyridine at room temperature, and 126 parts of methanesulfonyl chloride are added dropwise in the course of about 30 minutes, during which the temperature rises to 90°–95° C. After all the methanesulfonyl chloride has been added, the reaction mixture is refluxed for about 10 hours (temperature about 130°–135° C.). The working up is carried out as described in Example 1 and produces the same pyridinium compound in a similar space-time yield.

EXAMPLE 1c

A stirred flask is charged with 165.2 parts of N-ethyl-N-(2-hydroxyethyl)aniline and 261 parts of pyridine at room temperature, and 140.5 parts of benzenesulfonyl chloride are added dropwise in the course of 30 minutes. The temperature rises to 100° C. After all the benzenesulfonyl chloride has been added, the reaction mixture is refluxed for about 10 hours (temperature about 130°–135° C.). The working up is carried out as described in Example 1 and gives the same pyridinium compound in a similar space-time yield.

EXAMPLE 1d

A stirred flask is charged with 165.2 parts of N-ethyl-N-(2-hydroxyethyl)aniline and 261 parts of pyridine at 30° C., and 68.7 parts of phosphorus trichloride ($PCl_3$) are added dropwise in the course of 30 minutes. The temperature rises to 100° C. After all the $PCl_3$ has been added, the reaction mixture is refluxed for about 10 hours (temperature about 130°–135° C.). The working-up is carried out as described in Example 1 and gives the same pyridinium compound in a similar space-time yield.

EXAMPLE 1e

A stirred flask is charged with 165.2 parts of N-ethyl-N-(2-hydroxyethyl)aniline and 300 parts of dimethylformamide at room temperature, and 68.7 parts of phosphorus trichloride ($PCl_3$) are added dropwise in the course of 30 minutes. The temperature rises to 70°–75° C. After stirring at 80°–90° C. for two hours, 261 parts of pyridine are added, and the mixture is heated at 100°–110° C. for about 10 hours. The working-up is carried out as described in Example 1 and produces the same pyridinium compound in a similar space-time yield.

EXAMPLES 2–16

Example 1 is repeated using equivalent amounts of the hydroxyalkyl and nitrogen compound indicated in the Table. In each case, the corresponding cationic coupling components are obtained in a similar yield.

TABLE

| Example No. | Hydroxyalkyl compound | Nitrogen compound |
|---|---|---|
| 2 | N-Ethyl-N-(2-hydroxyethyl)aniline | p-Methylpyridine |
| 3 | N-Ethyl-N-(2-hydroxyethyl)aniline | m-Methylpyriding |
| 4 | N-Ethyl-N-(2-hydroxyethyl)aniline | o-Methylpyridine |
| 5 | N-Methyl-N-(2-hydroxyethyl)aniline | Pyridine |
| 6 | 2-Chloro-N-methyl-N-(2-hydroxyethyl)aniline | p-Methylpyridine |
| 7 | 3-Chloro-N-methyl-N-(2-hydroxyethyl)aniline | p-Methypyridine |
| 8 | 2,5-Dichloro-N-methyl-N-(2-hydroxyethyl)aniline | p-Methylpyridine |
| 9 | 2-Chloro-N-(2-hydroxethyl)aniline | Pyridine |
| 10 | 2-Chloro-N-(2-hydroxyethyl)aniline | p-Methylpyridine |
| 11 | 3-Methyl-N-ethyl-N-(2-hydroxyethyl)aniline | Pyridine |
| 12 | N,N-Di-(2-hydroxyethyl)aniline | Pyridine |
| 13 | 2-Chloro-N-(2-hydroxyethyl)aniline | p-Methylpyridine |
| 14 | N-Ethyl-N-(2-hydroxyethyl)aniline | 1-Dimethylamino-2-propanol |
| 15 | N-Ethyl-N-(2-hydroxyethyl)aniline | N-Methylmorpholine |
| 16 | N-Ethyl-N-(2-hydroxyethyl)aniline | N,N-Dimethylhydrazine |

What is claimed is:

1. A process for preparing a compound of the formula

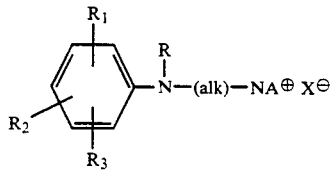

where
- $R_1$, $R_2$ and $R_3$ are each independently of the others hydrogen, $C_1$–$C_4$alkyl, $C_1$–$C_4$alkoxy, halogen or $C_1$–$C_4$alkanoylamino,
- R is hydrogen or unsubstituted or $C_1$–$C_4$alkoxy substituted $C_1$–$C_{12}$alkyl or an —(alk)—NA$^\oplus$X$^\ominus$ radical or,
- R and $R_1$ together with the N atom and the benzene ring form an unsubstituted or $C_1$–$C_4$alkyl-monosubstituted to -pentasubstituted dihydroindole, tetrahydroquinoline, tetrahydroquinoxaline or tetrahydro-1,4-benzoxazine radical,
- (alk) is unsubstituted or $C_1$–$C_4$alkoxy-, $C_1$–$C_4$alkanoyloxy-, $C_1$–$C_4$alkoxycarbonyl- or carbamoyl-substituted $C_1$–$C_6$alkylene,
- —NA$^\oplus$ is the radical of an amino compound of formula

or

where $R_4$, $R_5$ and $R_6$ are each independently of the others unsubstituted or hydroxyl-, $C_1$–$C_4$alkoxy, $C_1$–$C_4$alkanoyloxy-, $C_1$–$C_4$alkoxycarbonyl- or carbamoyl-substituted $C_1$-$C_6$alkyl or phenyl, benzyl or phenylethyl each unsubstituted or substituted by hydroxyl, $C_1$-$C_4$alkyl, $C_1$-$C_4$alkoxy, halogen, $C_1$-$C_4$alkanoylamino, $C_1$-$C_4$alkylsulfonyl, sulfamoyl, nitro, cyano or carbamoyl, $R_8$ and $R_9$ are each independently of the other unsubstituted or hydroxyl-, $C_1$-$C_4$alkoxy-, $C_1$-$C_4$alkanoyloxy-, $C_1$-$C_4$alkoxycarbonyl-or carbamoyl-substituted $C_1$-$C_6$alkyl, and $R_{10}$ and $R_{11}$ are each independently of the other hydrogen; unsubstituted or hydroxyl-, $C_1$-$C_4$alkoxy-, $C_1$-$C_4$alkanoyloxy-, $C_1$-$C_4$alkoxycarbonyl- or carbamoyl-substituted $C_1$-$C_6$alkyl; phenyl, benzyl, or phenylethyl each unsubstituted or substituted by hydroxyl, $C_1$-$C_4$alkyl, $C_1$-$C_4$alkoxy, halogen, $C_1$-$C_4$alkanoylamino, $C_1$-$C_4$alkylsulfonyl, sulfamoyl, nitro, cyano or carbamoyl;

or —NA$^\oplus$ is a positively charged radical of the formula

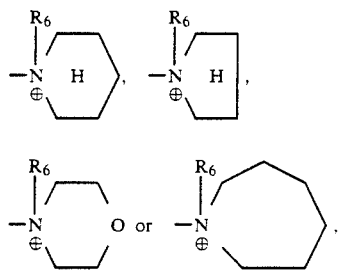

where $R_6$ is $C_1$-$C_4$alkyl; or an unsubstituted or $C_1$-$C_4$alkyl-, $C_1$-$C_4$alkoxy-, carbamoyl- or halogen-substituted positively charged pyrrole, indole, pyrazole, imidazole, benzimidazole, oxazole, benzoxazole, thiazole, benzothiazole, 1,2,4- or 1,3,4-thiadiazole, 1,2,3- or 1,2,4-triazole, benzotriazole, pyridine, pyrimidine, pyrazine, quinoline or isoquinoline radical, and $X^\ominus$ is a halide ion, which comprises reacting a compound of the formula

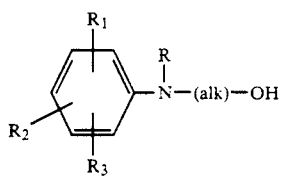

with a halogenating agent selected from the group consisting of $PX_3$, $PX_5$, $POX_3$, $SOX_2$, $SO_2X_2$, $R_{12}$—$SO_2$—X and

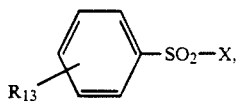

where X is halogen, $R_{12}$ is $C_1$-$C_4$alkyl and $R_{13}$ is hydrogen, $C_1$-$C_4$alkyl, $C_1$-$C_4$alkoxy, halogen or nitro, in the presence of a compound of the formula NA  (2a)

with liberation of an anion $X^\ominus$ and with R, $R_1$, $R_2$, $R_3$ and (alk) in the formula (3) each being as defined above and NA being the uncharged parent nitrogen compound to the radical —NA$^\oplus$.

2. A process according to claim 1 wherein R is hydrogen, methyl or ethyl.

3. A process according to claim 1, wherein (alk) is ethylene.

4. A process according to claim 1 wherein $X_1^\ominus$ is a chloride ion.

5. A process according to claim 1, wherein $R_1$, $R_2$ and $R_3$ are each independently of the others hydrogen, methyl, ethyl, methoxy, ethoxy, chlorine, acetylamino or propionylamino.

6. A process according to claim 1, wherein one of $R_1$, $R_2$ and $R_3$ is hydrogen and the other two are each independently of the other hydrogen, methyl, chlorine or acetylamino.

7. A process according to claim 1, wherein R is hydrogen or $C_1$-$C_4$alkyl.

8. A process according to claim 1, wherein (alk) is $C_2$-$C_4$alkylene.

9. A process according to claim 1, wherein —NA$^\oplus$ is a) a radical of the formula (2) shown in claim 1, where $R_4$, $R_5$ and $R_6$ are each independently of the others unsubstituted or hydroxyl-substituted $C_1$-$C_4$alkyl or unsubstituted or methyl-, methoxy-, chlorine- or acetylamino-substituted benzyl or phenyl, b) a radical of the formula

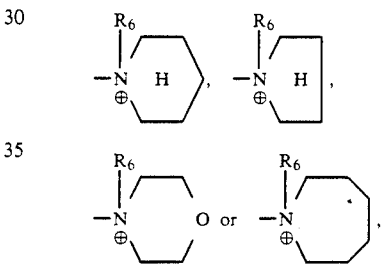

where $R_6$ is $C_1$-$C_4$alkyl, or c) an unsubstituted or $C_1$-$C_4$alkyl-, $C_1$-$C_4$alkoxy-, carbamoyl-or halogen-substituted positively charged pyrrole, indole, pyrazole, imidazole, benzimidazole, oxazole, benzoxazole, thiazole, benzothiazole, 1,2,4- or 1,3,4-thiadiazole, 1,2,3- or 1,2,4-triazole, benzotriazole, pyridine, pyrimidine, pyrazine, quinoline or isoquinoline radical.

10. A process according to claim 1, wherein —NA$^\oplus$ is a radical of the formula (2) shown in claim 1, where $R_4$, $R_5$ and $R_6$ are each independently of the others unsubstituted or hydroxyl-substituted $C_1$-$C_4$alkyl or unsubstituted or methyl-, methoxy-, chlorine- or acetylamino-substituted benzyl, or is a radical of the formula

where $R_7$ is hydrogen, methyl or carbamoyl.

11. A process according to claim 1, wherein —NA$^\oplus$ is pyridinium or o-, m- or p-methylpyridinium.

12. A process according to claim 1, wherein $X^\ominus$ is the chloride ion $Cl^\ominus$.

13. A process according to claim 1, wherein the halogenating agent used is $PCl_3$, $PCl_5$, $POCl_3$, methanesulfonyl chloride, benzenesulfonyl chloride, or p-toluenesulfonyl chloride, but in particular POCl$_3$.

14. A process according to claim 1, wherein the compounds of the formulae (2a) and (3) are introduced into a reaction vessel as initial charge, the halogenating agent is added, and the reaction is then allowed to go to completion.

15. A process according to claim 14, wherein the compounds of the formulae (2a) and (3) are used in a molar ratio of 2:1 to 5:1, preferably 2:1 to 3.5:1, at room temperature.

16. A process according to claim 14, wherein the halogenating agent is added in such a way that the temperature of the reaction mixture does not exceed 150° C.

17. A process according to claim 14, wherein, once the halogenating agent has been added, the reaction is allowed to go to completion at 75° to 150° C.

18. A process for preparing a compound of the formula (1) according to claim 1, where $R_1$, $R_2$ and $R_3$ are each independently of the others hydrogen, methyl, ethyl, methoxy, ethoxy, chlorine, acetylamino or propionylamino, R is hydrogen or $C_1$-$C_6$alkyl, (alk) is $C_2$-$C_4$alkylene, —NA$^\oplus$ is a) a radical of the formula (2) shown in claim 1 where $R_4$, $R_5$ and $R_6$ are each independently of the others unsubstituted or hydroxyl-substituted $C_1$-$C_4$alkyl or unsubstituted or methyl-, methoxy-, chlorine- or acetylamino-substituted benzyl or phenyl, b) a radical of the formula

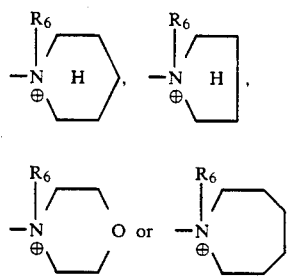

where $R_6$ is $C_1$-$C_4$alkyl, or c) an unsubstituted or $C_1$-$C_4$alkyl-, $C_1$-$C_4$alkoxy-, carbamoyl-or halogen-substituted positively charged pyrrole, indole, pyrazole, imidazole, benzimidazole, oxazole, benzoxazole, thiazole, benzothiazole, 1,2,4- or 1,3,4-thiadiazole, 1,2,3- or 1,2,4-triazole, benzotriazole, pyridine, pyrimidine, pyrazine, quinoline or isoquinoline radical, and X$^\ominus$ is an iodide, bromide or chloride ion, wherein a compound of the formula

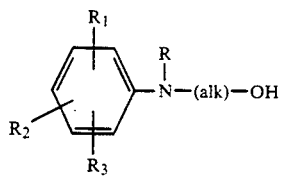

and a compound of the formula

NA (2a), where R, $R_1$, $R_2$, $R_3$ and (alk) are each as defined above and NA is the uncharged parent nitrogen compound to the radical —NA$^\oplus$, are introduced as initial charge into a reaction vessel at room temperature, a halogenating agent of the formula PX$_3$, PX$_5$, POX$_3$, SOX$_2$ or SO$_2$X$_2$, where X is iodine, bromine or chlorine is added in such a way that the temperature of the reaction mixture does not exceed 150° C., and the reaction is allowed to go to completion at 75° to 150° C.

19. A process for preparing a compound of the formula

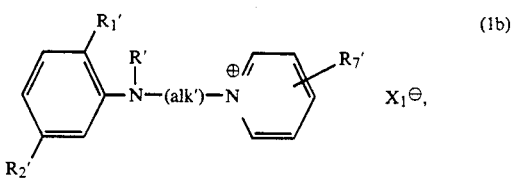

where $R_1'$ and $R_2'$ are each independently of the other hydrogen, methyl, chlorine or acetylamino, R' is hydrogen or $C_1$-$C_4$alkyl, (alk') is straight-chain or branched $C_2$-$C_4$alkylene, $R_7'$ is hydrogen or methyl, and $X_1^\ominus$ is a bromide or a chloride ion, which comprises introducing a compound of the formula

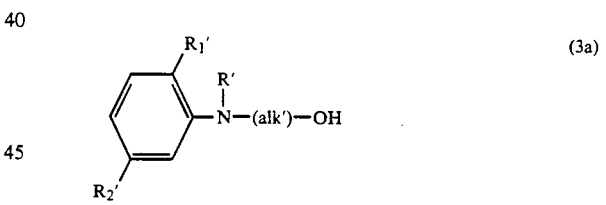

and a compound of the formula

as initial charge into a reaction vessel at room temperature, adding a halogenating agent POX$_3$ in such a way that the temperature of the reaction mixture does not exceed 150° C., and allowing the reaction to go to completion at 100° to 150° C., R', $R_1'$, $R_2'$, $R_7'$, (alk') and $X_1^\ominus$ being as defined above and X being bromine or chlorine.

* * * * *